United States Patent [19]
Borgens et al.

[11] Patent Number: 4,919,140
[45] Date of Patent: Apr. 24, 1990

[54] METHOD AND APPARATUS FOR REGENERATING NERVES

[75] Inventors: Richard B. Borgens, Delphi; Michael E. McGinnis, West Lafayette, both of Ind.

[73] Assignee: Purdue Research Foundation, West Lafayette, Ind.

[21] Appl. No.: 258,142

[22] Filed: Oct. 14, 1988

[51] Int. Cl.$^5$ .............................................. A61N 1/00
[52] U.S. Cl. .................................. 128/422; 128/421; 128/419 R; 128/784
[58] Field of Search .................... 128/421, 422, 419 F, 128/419 R, 783, 784

[56] References Cited

U.S. PATENT DOCUMENTS

| | | | |
|---|---|---|---|
| 3,817,254 | 6/1974 | Maurer | 128/421 |
| 3,893,462 | 7/1975 | Manning | 128/419 F |
| 4,084,595 | 4/1978 | Miller | 128/422 |
| 4,611,599 | 9/1986 | Bantall et al. | 128/422 |
| 4,774,967 | 10/1988 | Zanakis et al. | 128/785 |

OTHER PUBLICATIONS

McCaig, Colin D., "Spinal Neurite Reabsorption and Regrowth in vitro Depent on the Polarity of an Applied Electric Field,"*Development*, 100, 31-41, (1987).
Borgens, Richard B., A. Blight, D. Murphy & L. Stewart, "Transecte Dorsal Column Axons Within the Guinea Pig Spinal Cord Regenerate in the Presence of an Applied Electric Field," *Journal of Comparative Neurology*, 250:168-180, (1966).
Borgens, Richard B. A. Blight and M. McGinnis, "Behavioral Recovery Induced by Applied Electric Fields after Spinal Cord Hemisection in Guinea Pig," *Science*, 238:366-369, (Oct. 16, 1987).
Wallace, M. Christopher, C. Tator and I. Piper, "Recovery of Spinal Cord Function Induced by Direct Current Stimulation of the Injured Rat Spinal Cord," *Neurosurgery*, vol. 20, No. 6, Part I, (1987).
Politis, Michael J. and Michael F. Zanakis, "Short Term Efficacy of Applied Electric Fields in the Repair of the Damaged Rodent Spinal Cord: Behavioral and Morphological Results".
M. F. Zanakis and M. J. Politis, "Short Term Bahavioral and Histological Changes in the Damaged Rat Spinal Cord Following Application of D.C. Electric Fields," (Abstract).
M. Khan, M. J. Politis and D. Munoz-Garcia, "The Effect of Localized Oriented Electric Fields on Regenerative Changes in Double Hemisectioned Spinal Cord of Rats," Canadian Congress of Neurological Sciences, Jun. 25-27, 1987, (Abstract).
Berry, M., "Regeneration in the Central Nervous System," *Recent Advances in Neuropathology*, Ch. 4, (1st ed. 1979), (Editors: W. T. Smith and V. B. Cavanaugh).
Kiernan, J., "Hypotheses Concerned with Axonal Regeneration in the Mammalian Nervous System," Biol. Rev., 54:155-197, (1979).
Borgens, Richard E. and Michael E. McGinnis, "Artificially Controlling Axonal Regeneration and Development by Applied Electric Fields," Chapter 4, *Electric Fields in Vertebrate Repair*, (1989).
"Final Thrusts Prepared in RES," *Spinal Cord Society Newsletter, pp. 3-4, (Jun. 1987)*.

*Primary Examiner*—Francis Jaworski
*Assistant Examiner*—George Manuel
*Attorney, Agent, or Firm*—Barnes & Thornburg

[57] ABSTRACT

A method and apparatus for stimulating nerves in the central nervous system of a mammal to regenerate within the central nervous system applies an oscillating electrical field to the central nervous system across a lesion in the central nervous system. The polarity reversal period of the electrical field is long enough to stimulate growth of cathodally facing axons of the nerve cells in the central nervous system but is shorter than a die back period of anodally facing axons of the nerve cells.

11 Claims, 2 Drawing Sheets

METHOD AND APPARATUS FOR REGENERATING NERVES

This invention relates to a method and apparatus for causing nerves to regenerate, particularly, nerves in the central nervous system of mammals.

Injury to the spinal cord or central nervous system can be one of the most devastating and disabling injuries possible. Depending upon the severity of the injury, paralysis of varying degrees can result. Paraplegia and quadriplegia often result from severe injury to the spinal cord. The resulting effect on the sufferer, be it man or animal, is severe. The sufferer can be reduced to a state of near immobility or worse. For humans, the mental trauma induced by such severe physical disability can be even more devastating than the physical disability itself.

Heretofore, it has been long thought that once damaged, the nerves of the central nervous system in mammals do not regenerate and cannot be caused to regenerate within the environment of the central nervous system. Any regeneration of injured nerves in the central nervous system of mammals has been found to occur, if at all, only within a very short period immediately after the injury occurs. After this short period expires, such nerves have not been found to regenerate.

This is in marked contrast to nerves outside the central nervous system in mammals, i.e., nerves in the peripheral nervous system and even to nerves in the central nervous system of lower order vertebrates, not to mention invertebrates. Nerves in the peripheral nervous system of mammals are known to regenerate spontaneously. Further, past studies have shown that the regeneration of nerves in the peripheral nervous system of mammals can be stimulated by the application of electrical fields. Similar past studies have also shown that regeneration of nerves in the central nervous system of lower order vertebrates, such as lampreys, can be stimulated by the application of electrical fields. Past studies have also shown that if nerves from a spinal cord of a mammal are taken out of the central nervous system environment and placed in a peripheral nervous system environment, the nerves will in fact regenerate. In one such study, it was found that axons from central nervous system neurones would regenerate into peripheral nervous system grafts. (P. Richardson, V. McGuiness, and A. Aguaso, "Axons From CNS Neurones Regenerate into PNS Grafts," Nature, 284, 264–286)

More recently, it was disclosed that a steady state DC electrical field would stimulate axons to grow into the glial scar in guinea pigs having partially several spinal cords. (R. Borgens, A. Blight, D. Murphy and L. Stewart, "Transected Dorsal Column Axons Within the Guinea Pig Spinal Cord Regenerate in the Presence of an Applied Electrical Field," Journal of Comparative Neurology, 250: 168-180 (1986). However, although such an electrical field stimulates axon growth in one direction, i.e., axons facing the cathode, it not only will retard axon growth in the opposite direction, i.e., anodal facing axons, but will actually cause anodal facing axons to reabsorb into the bodies of their nerve cells.

In a study involving embryonic spinal neurites (axons) of frogs, it was found that while the application of a steady state DC electrical field would stimulate neurite growth toward the cathode almost immediately, reabsorption of anodal facing neurites would begin to occur only after a period of time elapsed. (C. McCaig, "Spinal Neurite Reabsorption and Regrowth In Vitro Depend on the Polarity of an Applied Electric Field," Development 100, 31"(May, 1987). This study found that the rate of reabsorption began slowly and increased as time elapsed. The maximal phase of retraction (reabsorption) of anodal facing neurites was found to take place over a twenty minute period roughly one hour after the onset of reabsorption. This study also disclosed that when the polarity of the electrical field was reversed, reabsorption of the previously anodal facing neurites was halted and neurite growth was stimulated in that direction. In contrast, growth of the previously cathodal facing neurites was halted and these neurites began to reabsorb after a period of time. The study concluded by stating that reabsorption induced by an electrical field was found to be most severe within one to one and one half hours after the field was applied whereas regeneration was promoted optimally within twenty minutes after the electrical field was reversed. The study then postulated that if the results reflected what might happen in vivo, then an optimal regime for electrical stimulation across a lesion might be to alternate the polarity of the electrical field every half hour to one hour, ensuring that the electric field was applied early on before excessive die-back of axons occurred.

Even with the results of these most recent studies, conventional thinking remains that nerves in the central nervous system of mammals will not regenerate within the central nervous system environment and cannot be caused to regenerate. Applicants, however, have found that by applying an oscillating electrical field to the central nervous system of a mammal, the nerves in the central nervous system can be stimulated to regenerate within the central nervous system. By oscillating electrical field it is meant that a DC electrical field is imposed in one direction for a period of time to promote growth in one direction and the polarity of the field then reversed before die back of the oppositely facing axons begins or becomes significant.

It is an object of this invention to stimulate nerves in the central nervous system of mammals to regenerate within the central nervous system.

In accordance with this invention, the nerves in the central nervous system of a mammal are stimulated to regenerate by applying an oscillating electrical field to the central nervous system. The oscillating electrical field is illustratively a constant current DC field the polarity of which is reversed after a predetermined time. The predetermined time is set to be less than the die-back period of anodal facing axons.

Additional features and advantages of the invention will become apparent to those skilled in the art upon consideration of the following detailed description of a preferred embodiment, exemplifying the best mode of carrying out the invention as presently perceived. The detailed description particularly refers to the accompanying figures in which.

Figure 1:
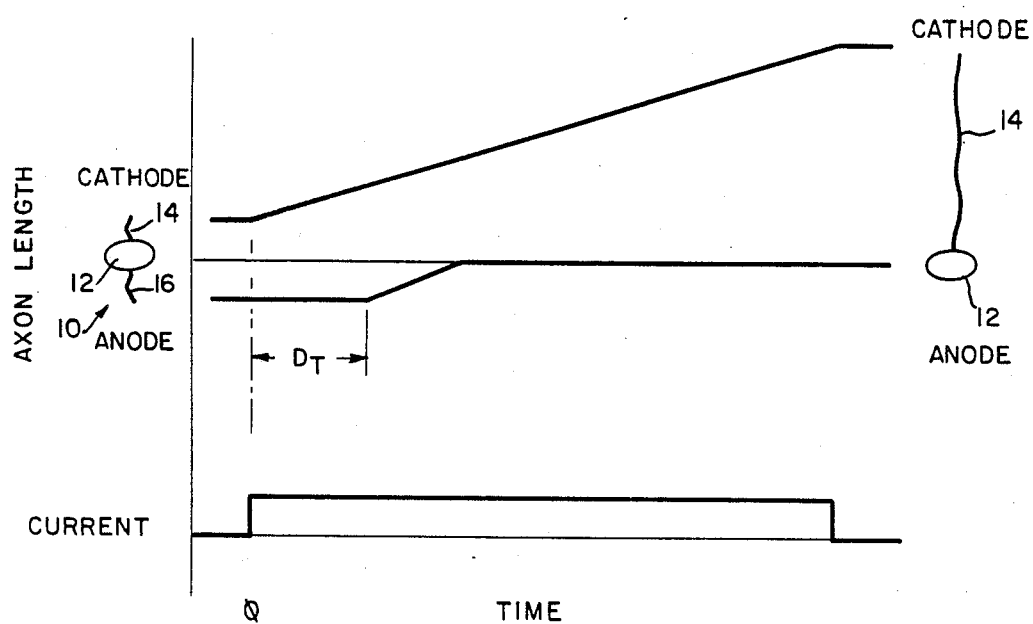
FIG. 1 is a graph which shows the effect of an applied steady DC field over time on the growth of cathodal and anodal facing axons.

In accordance with this invention, nerves in the spinal cord of a mammal are stimulated to regenerate within the spinal cord by the application of an oscillating electrical field to the spinal cord. The oscillating electrical field is a constant current DC stimulus which is first applied in one direction for a predetermined period of time and then applied in the opposite direction for the predetermined period of time. In other words, the polarity of the constant current DC stimulus is reversed after each predetermined period of time. The predetermined period of time, which is the time period of one half-cycle of the oscillating electrical field, is selected to be less than the die back period of anodal facing axons but long enough to stimulate growth of cathodal facing axons. Applicants believe that in mammals, this predetermined period will need to be at least thirty seconds to stimulate growth of cathodal facing axons. This predetermined period will be termed the "polarity reversal period" of the oscillating electrical field.

When the spinal cord of a mammal is injured, connections between nerves in the spinal cord are broken. Conventionally, the injured portion of the spinal cord is termed a lesion. Such lesions block the flow of nerve impulses for the nerve tracts affected by the lesion with resulting impairment to both sensory and motor function.

To restore the lost sensory and motor functions, the affected motor and sensory axons of the injured nerves must regenerate, that is, grow back. Unfortunately, this has not been found to occur in the spinal cord of mammals. Applicants, however, have found that by applying a DC electrical field across a lesion in the spinal cord of mammals, axon growth can be promoted and the axons will grow back around the lesion. Since the spinal cord is rarely severed completely when injured, the axons need not actually grow across the lesion but can circumnavigate the lesion through remaining spinal cord parenchyma. However, such findings have met with widespread disbelief. Conventional thinking remains that the nerves in the spinal cord of mammals will not regenerate within the spinal cord and cannot be caused to do so.

Although it has been known that axon growth can be promoted in the peripheral nervous system of mammals and in the central nervous system of lower order vertebrates by the application of a steady DC electrical field, only those axons facing the cathode (negative pole) are stimulated to grow. Axons facing the anode (positive pole) not only are not stimulated to grow, but actually reabsorb into the bodies of the nerve cells ("die back)," after a period of time. As discussed previously, McCaig has found that significant die back or reabsorption of anodal facing axons begins to occur about one hour after the DC electrical field is applied. The period of time which elapses from when a DC electrical field is first applied to when significant reabsorption or die back of the anodal facing axons begins will be termed the "die back period." McCaig's experiments were conducted using embryonic spinal cord cells of frogs.

In order to "repair" an injured spinal cord, regeneration of both the ascending and descending nerve tracks must be promoted. Thus, axons growth in both directions, i.e., rostrally and caudally, must be stimulated to "repair" an injured spinal cord. Applicants have found that applying an oscillating electrical field across a lesion in the spinal cord of a mammal will stimulate axon growth in both directions, i.e., caudally and rostrally. That is, growth of caudally facing axons will be promoted as will growth of rostrally facing axons.

Figure 2:
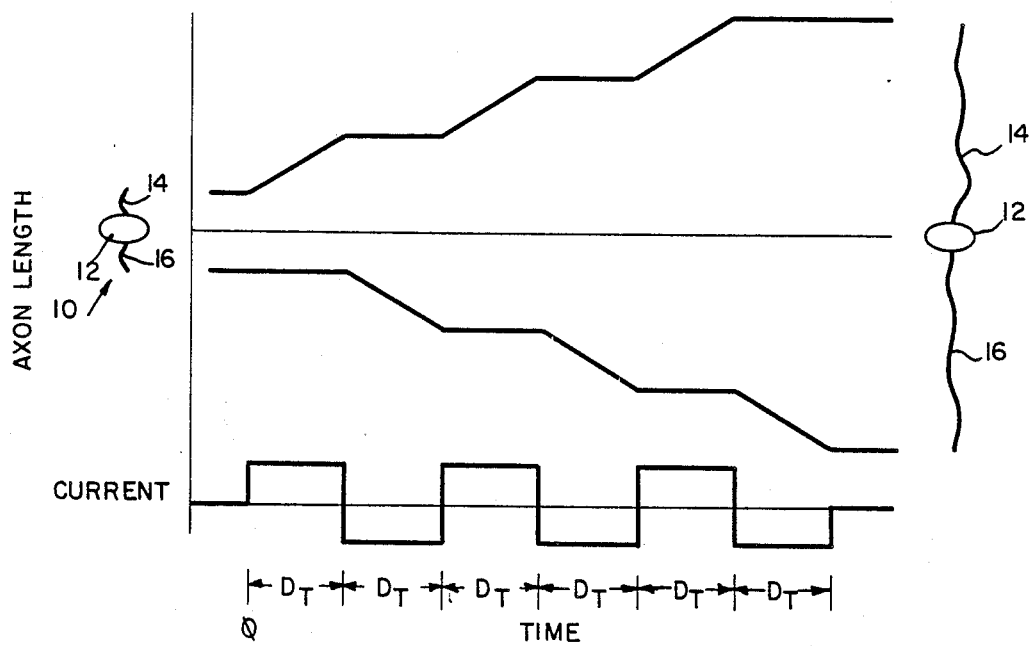
FIG. 2 is a graph which shows the effect of an applied oscillating field over time on the growth of cathodal and anodal facing axons.

FIGS. 1 and 2 show the affects on axon growth by an applied steady state DC electrical field (FIG. 1) and by an applied oscillating electrical field (FIG. 2). Referring to FIG. 1, a nerve cell 10 is shown at the left-hand side of FIG. 1 having a cell body or soma 12 from which an axon 14 extends upwardly and an axon 16 extends downwardly. At time 0, a constant current DC stimulus is applied to the nerve cell 10 such that axon 14 will be extending toward the cathode or negative pole of a DC stimulus signal and axon 16 will be extending toward the anode or positive pole of the DC stimulus. Axon 14 begins to grow almost immediately. However, after a period of time, i.e., the "die back period" ($D_T$), significantly reabsorption of axon 16 into the cell body 12 begins and eventually axon 16 is completely reabsorbed into cell body 12. At the right hand of FIG. 1 nerve cell 10 is shown wherein axon 14 has grown substantially longer but axon 16 has been reabsorbed into cell body 12.

In FIG. 2, the same reference numbers will be used to identify the elements of FIG. 2 which correspond to elements of FIG. 1. Nerve cell 10 is shown at the left-hand side of FIG. 2 having a cell body 12, an upwardly extending axon 14 and a downwardly extending axon 16. At time 0, a constant current DC stimulus is applied to nerve cell 10 such that axon 14 is extending toward the cathode ad axon 16 is extending toward the anode of the DC stimulus. After a predetermined period of time, the polarity of the DC stimulus is reversed. Axon 14 will now be extending toward the anode and axon 16 will be extending toward the cathode of the DC stimulus. The predetermined period of time is selected to be less than the die back period ($D_T$) of the anodal facing axon. As has been discussed, significant die back of anodal facing axons begins to occur about one hour after the DC stimulus is applied. Therefore, the predetermined period should not exceed one hour. As shown in FIG. 2, this oscillating field stimulates growth of the axons facing both direction. This is due to the fact that growth of cathodal facing axons is stimulated almost immediately after the DC stimulus is applied but die back of the anodal facing axons does not become significant until after the die back period elapses. Since the polarity of the DC stimulus is switched before the die back period elapses, growth of axons in both directions is stimulated with the result that axons 14, 16 of nerve cell 12 both grow significantly longer as shown at the right-hand side of FIG. 2.

Figure 3:
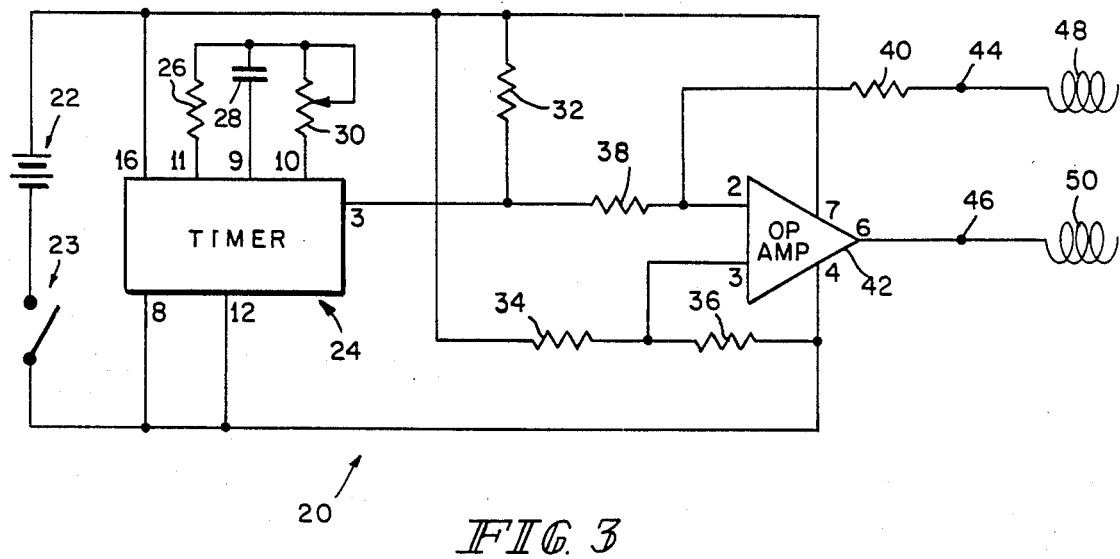
FIG. 3 is a schematic of a circuit for generating an oscillation electrical field for stimulating nerve regeneration.

FIG. 3 is a schematic of a circuit for generating an oscillating field for application to the spinal cord of a mammal to stimulate nerve regeneration. Generator 20 includes a six volt battery 22, a power switch 23, a time 24, 6.2M resistor 26, 0.047 µF capacitor 28, 2M potentiometer 30, 1M resistors 32, 34, 36, 15K resistor 38, 1K resistor 40, and low power operational amplifier 42. Illustratively, timer 24 is a 14-stage ripple counter and oscillator chip such as a CD4060BE and low power operational amplifier 42 is an ICL7611 low power CMOS operational amplifier, both of which are manufactured by RCA. Battery 22 illustratively comprises two series connected three volt lithium dioxide battery cells such as DL2025 battery cells manufactured by Duracell.

The positive terminal of battery 22 is coupled to the V+ terminal (pin 16) of the 14-stage ripple counter and oscillator chip which is timer 24 and to the V+ terminal (pin 7) of operational amplifier 42. Resistor 26, capacitor 28 and potentiometer 30 are used to set the frequency of the oscillator of the 14-stage ripple counter and oscillator chip. One terminal of resistor 26 is coupled to the clock input (pin 11) of timer 24 and its other terminal is coupled to a first terminal of capacitor 28 and to a first terminal of potentiometer 30. The first terminal of potentiometer 30 is also coupled to the wiper terminal of potentiometer 30. A second terminal of capacitor 26 is coupled to a first frequency set output (pin 9) of timer 24 and a second terminal of potentiometer 30 is coupled to a second frequency set output (pin 10) of timer 24. The V— terminal (pin 8) of timer 24 is coupled to a first terminal of switch 23. A second terminal of switch 23 is coupled to the negative terminal of battery 22. A reset input (pin 12) of timer 24 is also coupled to the first terminal of switch 23 as is the V— terminal (pin 4) of operational amplifier 42.

An output (pin 3) of timer 24 is coupled through resistor 32 to the positive terminal of battery 22 and through resistor 38 to the negative input (pin 2) of operational amplifier 42. The positive input (pin 3) of operational amplifier 42 is coupled through resistor 34 to the positive terminal of battery 22 and through resistor 36 to the first terminal of switch 23. The negative input (pin 2) of operational amplifier 42 is coupled through resistor 40 to an output terminal 44. The output (pin 6) of operational amplifier 42 is coupled to an output terminal 46.

Output terminal 44 of stimulator 20 is coupled to an electrode 48 and output terminal 46 is coupled to an electrode 50. Illustratively, electrodes 48, 50 comprise silastic insulated platinum electrodes.

When power switch 23 is closed, generator 20 generates an oscillating electrical field at output terminals 44, 46. That is, generator 20 generates a constant current DC stimulus the polarity of which is reversed periodically after the expiration of a predetermined period of time determined by timer 24. Output terminals 44, 46 will thus alternately comprise cathode and anode terminals, respectively, of generator 20 depending upon the polarity of the DC stimulus.

The predetermined period of time determined by timer 24 is set by the frequency of the oscillator in the 14-stage ripple counter and oscillator chip which is timer 24. Potentiometer 30 is used to set the frequency of the oscillator in the 14-stage ripple counter and oscillator chip. The output of this oscillator can then be divided by up to 14 binary stages by the 14-stage ripple counter and oscillator chip to achieve very low frequency oscillations. If the frequency of this oscillator is illustratively set to 4.5 Hz and divided by these 14 binary stages, a frequency of one cycle per hour at the output (pin 3) of the 14-stage ripple counter and oscillator chip (timer 24) is produced which causes generator 20 to reverse polarity every thirty minutes. Applicants have found that a polarity reversal every fifteen minutes is effective to stimulate nerve regeneration in dogs, although a longer period would be more effective though possibly less safe. In guinea pig studies, applicants have used a polarity reversal period of thirty minutes to effectively stimulate nerve regeneration.

The output of timer 24 is taken from the appropriate binary stage of the 14-stage ripple counter and oscillator chip, which, in the embodiment shown, is the output of the fourteenth stage (pin 3) and is a square wave oscillator between 0 VDC and 6 VDC (railed at the supply voltage) with a frequency determined as described above. This square wave is applied to the inverting input (pin 2) of operational amplifier 42. Resistors 34, 36, illustratively being equal, set up a 3 VDC reference voltage at the positive input (pin 3) of operational amplifier 42. Therefore, depending on whether the output of timer 24 is high or low, there will be a net +3 VDC or −3 VDC at the inverting input of operational amplifier 42 which drives current through electrodes 48, 50.

The magnitude of the current sourced by generator 20 is determined by the value Rc in the equation:

$$I = \frac{3V}{Rc}$$

where Rc is resistor 38 and the 3V is determined by the net voltage differential between the inverting and non-inverting inputs of operational amplifier 42.

If generator 20 is to source currents less than 100 $\mu$A, the quiescent current of operational amplifier 42 is set to 1 $\mu$A by strapping its pin 8 to +V. If generator 20 is to source more than 100 $\mu$A, the quiescent current of operational amplifier 42 is set to 10 $\mu$A by letting pin 8 float.

The current sourced by generator 20 is selected to provide sufficient field strength in the section of the spinal cord in which nerve regeneration is to be stimulated. Applicants have found that a field strength of 200 $\mu$V/mm in the spinal cord will stimulate regeneration. The current needed to achieve this field strength is determined, such as by experiment, by the geometry of the animal in which generator 20 is used. Applicants have found that a current of 20 $\mu$A will provide a sufficient field strength to stimulate nerve regeneration in the spinal cords of guinea pigs whereas a current of about 200 $\mu$A is needed to provide sufficient field strength to stimulate nerve regeneration in the spinal cords of dogs weighing approximately twenty to thirty pounds.

Power switch 23 is used to disconnect power to generator 20 until generator 20 is ready to be used. Timer 24 draws approximately 45 $\mu$A and to prevent this power drain from occuring prematurely, power switch 23 is used to keep power disconnected until generator 20 is put in use. Preferably, generator 20 is packaged in a sealed package since it will preferably be implanted in a subject. To permit power switch 20 to be actuated when it is enclosed within such a sealed package, power switch 23 is illustratively a normally closed magnetic reed switch. A magnet is then detachably affixed to the packaged generator 20 to hold switch 23 open until generator 20 is ready for use. The magnet is then removed permitting the magnetic red switch which is power switch 23 to close. Alternatively, power switch 23 could be a latching magnetic reed switch. Power switch 23 could also be a sealed mechanical switch which can be actuated from outside the sealed package of generator 20. Finally, power switch 23 could be dispensed with altogether and either the positive or negative terminal of battery 22 left disconnected until generator 20 is ready for use. At that time, the terminal would be connected. This would, of course, require that the package in which generator 20 is placed be left open to some extent and sealed up at this time.

Electrodes 48, 50 are implanted on opposite sides of a lesion in the spinal cord, respectively. Applicants have found that it is sufficient to implant electrodes 48, 50 in a laminectomy adjacent the spinal cord but not actually in the spinal cord. Further, in studies involving the application of a steady state DC electrical field, applicants have found that moving the anode from within the laminectomy to a site on the muscle dorsal to the same area results in only about a ten percent drop in field strength as does the converse of moving the cathode to a more superficial position while leaving the anode in the laminectomy. Further, uniform field homogeneity can be achieved by locating the electrodes anywhere on the midline of the spinal cord, including locating both electrodes on the same side of the lesion but spaced apart, although locating the electrodes on opposite sides of the lesion is preferred.

Applicants have also found that the field strength within the spinal cord at the site of the lesion depends upon the location of the current delivery electrodes. The convergence of current to an electrode produces high current density and hence higher field strength near each electrode. The closer one electrode is to the lesion site, the less critical is the placement on the other to maintain high field strengths. However, as a current delivery electrode approaches the lesion, current direction becomes less uniform. At a lesion exactly half-way between two electrodes placed on the midline, the current will all be oriented along the long axis of the subject animal. As one of the electrodes is moved closer to the lesion, there will be a larger vertical (dorsal-ventrical) component of the current at the lesion (assuming that the electrodes remain a few millimeters dorsal to the target tissue). As a compromise between uniform current direction and maximum field strength, applicants have chosen to position the electrodes two vertebral segments on either side of the lesion in their spinal cord studies. In the guinea pig studies applicants have conducted, it appears that the critical distance to be within one convergence zone of an electrode (that area in which the current convergence to the electrode so dominates the field strength that the position of the other electrode is relatively inconsequential) is approximately 1 cm. Therefore, by placing one electrode within 1 cm of the lesion, the position of the other becomes relatively inconsequential and becomes a matter of convenience. It should be noted, however, that the electrodes can be located further from the lesion. If they are, the field strength of the electrical field at the lesion for a given magnitude of current will be reduced. Therefore, the magnitude of the current would have to be increased to yield the same electrical field strength at the lesion.

In addition to promoting axon growth in both directions, use of an oscillating electrical field also reduces the production of electrode products which alter the pH of the environment surrounding the electrode. Applicants have found that after twenty-four hours of application of a constant 35 µA of a steady state DC electrical field, the pH at the cathode well (environment surrounding the cathode electrode) was 9.8 and the pH at the anode well was 3.4. After 48 hours, the pH at the anode well was 2.4. In contrast, after 60 hours of application of an oscillating electrical field where the polarity of the DC stimulus was reversed every forty-five minutes, the largest pH change at either well was 0.4 pH units.

Although the invention has been described in detail with reference to certain preferred embodiments and specific examples, variations and modifications exist within the scope and spirit of the invention as described and as defined in the following claims.

What is claimed is:

1. A method for stimulating nerves in the central nervous system of a mammal to regenerate within the central nervous system comprising the step of applying an oscillating electrical field to the spinal cord wherein the electrical field's polarity reversal period is less than about sixty minutes which is less than a die back period of anodally facing axons in the central nervous system and more than about thirty seconds which is long enough to stimulate growth of cathodally facing axons in the central nervous system.

2. A method for stimulating axon growth in the spinal cord of a mammal to stimulate nerve regeneration comprising the step of applying an oscillating electrical field across a lesion in the spinal cord wherein the oscillating electrical field's polarity reversal period is long enough to stimulate growth of cathodally facing axons in the spinal cord but is less than a die back period of anodally facing axons in the spinal cord.

3. The method of claim 2 wherein the polarity reversal period of the oscillating electrical field is in the range of thirty seconds to sixty minutes.

4. A method for stimulating nerves in the central nervous system of a mammal to regenerate within the central nervous system comprising the steps of implanting electrodes on opposite sides of a lesion, generating an oscillating electrical field that has a polarity reversal period in the range of about thirty seconds to about sixty minutes, and applying the oscillating electrical to the electrodes to apply the oscillating electrical field to the central nervous system.

5. A method for stimulating nerves in the central nervous system of a mammal to regenerate, said nerves having nerve cells with caudally extending axons and rostrally extending axons, comprising the steps of applying a constant current DC stimulus to the central nervous system and reversing the polarity of the DC stimulus after a predetermined period of time which is in the range of about thirty seconds to about sixty minutes.

6. The method of claim 5 wherein the polarity of the DC stimulus is reversed each time the predetermined period of time elapses.

7. An apparatus for stimulating nerves in the central nervous system of a mammal to regenerate within the central nervous system, comprising means for generating an oscillating electrical field which as a polarity reversal period long enough to stimulate growth of cathodally facing axons of the nerves to be stimulated but less than a die back period of anodally facing axons of the nerves to be stimulated and means for coupling an output of the generating means to the central nervous system.

8. The apparatus of claim 7 wherein the output of the generating means has first and second oppositely polarized output terminals and the means for coupling the output of the generating means to the central nervous system comprises first and second electrodes coupled respectively to the first and second outputs of the generating means.

9. The apparatus of claim 8 wherein the means for generating the oscillating electrical field generates the oscillating electrical field with a polarity reversal period in the range of thirty seconds to sixty minutes.

10. An apparatus for stimulating axon growth of the nerve cells in the spinal cord of mammals to stimulate regeneration of the nerve cells in the spinal cord, comprising means for generating a constant current DC stimulus, the generating means having first and second oppositely polarized output terminals wherein one output terminal comprises a cathode and the other output terminal comprises an anode of the generating means, means for coupling the first and second output terminals to the spinal cord on opposite sides of a lesion, and means for reversing the polarity of the DC stimulus each time a predetermined period of time elapses, the predetermined time period being in the range of about thirty seconds to sixty minutes, and wherein each time the polarity of the DC stimulus is reversed the output terminal which comprised the cathode before the polarity reversal comprises the anode after the reversal and the output terminal which comprised the anode before the polarity reversal comprises the cathode after the polarity reversal.

11. The apparatus of claim 10 wherein the means for coupling the first and second output terminals to the spinal cord comprises first and second electrodes coupled respectively to the first and second output terminals.

* * * * *